United States Patent
Baumann

(10) Patent No.: US 12,108,128 B2
(45) Date of Patent: Oct. 1, 2024

(54) APPARATUS, SYSTEM AND METHOD TO CAPTURE IMAGES OF A MEDICAL SITE IN WHITE LIGHT AND FLUORESCENT LIGHT

(71) Applicant: KARL STORZ SE & Co KG, Tuttlingen (DE)

(72) Inventor: Christin Baumann, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 214 days.

(21) Appl. No.: 17/547,844

(22) Filed: Dec. 10, 2021

(65) Prior Publication Data

US 2022/0191439 A1 Jun. 16, 2022

(30) Foreign Application Priority Data

Dec. 10, 2020 (DE) .......................... 102020132951.2

(51) Int. Cl.
*H04N 23/16* (2023.01)
*A61B 5/00* (2006.01)
(Continued)

(52) U.S. Cl.
CPC ........... *H04N 23/16* (2023.01); *A61B 5/0071* (2013.01); *A61K 49/0021* (2013.01);
(Continued)

(58) Field of Classification Search
CPC ......... H04N 23/16; H04N 23/72; H04N 23/45
See application file for complete search history.

(56) References Cited

U.S. PATENT DOCUMENTS

2004/0225222 A1* 11/2004 Zeng .......................... G01J 3/32
600/476
2011/0104071 A1* 5/2011 Lee ....................... A61B 5/0084
530/331
(Continued)

FOREIGN PATENT DOCUMENTS

DE 102015011441 A1 3/2017
DE 102017203448 A1 9/2018
(Continued)

OTHER PUBLICATIONS

Mieog, J. S. D., S. L. Troyan, M. Hutteman, et al., "Toward Optimization of Imaging System and Lymphatic Tracer for Near-Infrared Fluorescent Sentinel Lymph Node Mapping in Breast Cancer," Annals of Surgical Oncology, 2011, pp. 2483-2491+ supplemental, 18, Springer Nature, Swizerland.
(Continued)

*Primary Examiner* — Hugh Maupin
(74) *Attorney, Agent, or Firm* — David N. Villalpando; Jacqueline Cohen

(57) ABSTRACT

A device for capturing an image of an object of medical interest in remitted or reflected illumination light and for capturing an image of the object in fluorescent light generated by Cy5.5 and/or SGM-101 and for capturing an image in fluorescent light generated OTL38 and/or indocyanine green (ICG). The device includes an image sensor for detecting blue, green and red light, another image sensor for
(Continued)

detecting fluorescent light of Cy5.5 and/or SGM-101 and OTL38 and/or ICG, a beam splitter guiding light having a wavelength smaller than a predetermined cutoff wavelength to the first sensor and guiding light having a wavelength greater than the predetermined cutoff wavelength to the second sensor, and filters upstream of the second sensor for partially, substantially or completely suppressing light having a wavelength exciting Cy5.5 and/or SGM-101 and for partially, substantially or completely suppressing light having a wavelength suitable for exciting fluorescence of OTL38 and/or ICG.

3 Claims, 4 Drawing Sheets

(51) Int. Cl.
A61K 49/00 (2006.01)
H04N 9/68 (2023.01)
H04N 23/45 (2023.01)
H04N 23/72 (2023.01)

(52) U.S. Cl.
CPC ...... A61K 49/0032 (2013.01); A61K 49/0034 (2013.01); A61K 49/0058 (2013.01); H04N 9/68 (2013.01); H04N 23/45 (2023.01); H04N 23/72 (2023.01)

(56) References Cited

U.S. PATENT DOCUMENTS

| | | | |
|---|---|---|---|
| 2017/0167980 A1 | 6/2017 | Dimitriadis et al. | |
| 2017/0176336 A1 | 6/2017 | Dimitriadis et al. | |
| 2018/0196246 A1* | 7/2018 | Bares | G01J 3/0208 |
| 2019/0170647 A1 | 6/2019 | Ikenaga et al. | |
| 2020/0363338 A1* | 11/2020 | Almogy | G02B 21/30 |
| 2021/0219847 A1* | 7/2021 | Bernat | A61B 5/0205 |
| 2021/0307613 A1* | 10/2021 | Fengler | H04N 23/56 |
| 2021/0341389 A1* | 11/2021 | Wang | G01N 21/6486 |

FOREIGN PATENT DOCUMENTS

| | | |
|---|---|---|
| WO | 2016185661 A1 | 12/2016 |
| WO | 2017036600 A1 | 3/2017 |
| WO | 2020052626 A1 | 3/2020 |

OTHER PUBLICATIONS

Troyan, S. L., V. Kianzad, S. L. Gibbs-Strauss, et al., "The FLARE Intraoperative Near-Infrared Fluorescence Imaging System: A First-in-Human Clinical Trial in Breast Cancer Sentinel Lymph Node Mapping," Annals of Surgical Oncology, 2009 pp. 2943-2952, 16, Springer Nature, Swizerland.

Baust, "Prüfungsbescheid (German Report on Patentability)," Nov. 25, 2021, pp. 1-7, German Patent Office, Munich.

* cited by examiner

APPARATUS, SYSTEM AND METHOD TO CAPTURE IMAGES OF A MEDICAL SITE IN WHITE LIGHT AND FLUORESCENT LIGHT

CROSS REFERENCE TO RELATED APPLICATIONS

This application claims priority to German Patent Application No. 102020132951.2, filed Dec. 10, 2020, and entitled, "Capture of images of a medical site in white light and fluorescent light," and is incorporated herein by reference.

TECHNICAL FIELD OF THE INVENTION

The present invention relates to a device, system, and method for capturing images of an object of medical interest in a medical site in remitted or reflected light and in fluorescent light.

BACKGROUND OF THE INVENTION

In some diagnostic imaging procedures, an image of an object of medical interest (sometimes herein referred to simply as "an object" or "an object of interest") illuminated with white light and an image of the object in fluorescent light are captured by one or more image sensors simultaneously or successively.

A modern fluorophore is Cy5.5, which is excited with light in the wavelength range of 660 nm to 690 nm (red; absorption maximum at 675 nm) and emits fluorescent light in the wavelength range of 680 nm to 720 nm (emission maximum at 694 nm or 707 nm). Another fluorophore is SGM-101, which is excited with light in the wavelength range of 660 nm to 700 nm (red; absorption maximum at 680 nm or 685 nm) and emits fluorescent light in the wavelength range of 690 nm to 720 nm (emission maximum at 705 nm). Another fluorophore is OTL38, which is excited with light in the wavelength range of 760 nm to 790 nm (red; absorption maximum at 774 nm or 776 nm) and emits fluorescent light in the wavelength range of 780 nm to 810 nm (emission maximum at 793 nm or at 794 nm to 796 nm). Another commonly used fluorophore is indocyanine green (ICG), which is excited with light in the wavelength range of 700 nm to 850 nm (red to infrared; absorption maximum at 830 nm) and emits fluorescent light in the wavelength range of 780 nm to 870 nm (emission maximum at 830 nm).

Two cameras, or image sensors, can be used to detect remitted white light and fluorescent light. A first camera captures the image resulting from the illumination of the object with white light in the visible spectral range, a second camera captures the emitted fluorescent light. Both cameras can, for example, be coupled to a single endoscope or optical system via dichroic reflecting surfaces to capture both images from the same perspective.

WO 2015/185661 A1 describes the alternating illumination of an object with light of different spectra and the synchronous alternating capture of images of the object with a common image sensor (page 6, last paragraph, to page 7, fifth paragraph, FIGS. 1, 2). In a phase 1, the object is illuminated with light with a spectrum comprising several high intensity ranges and a low intensity range comprising longer wavelengths than a high intensity range. In a phase 2, the object is illuminated with light having a broad spectrum. In both phases, light emitted or remitted from the object is detected with the same image sensor. In phase 1, the spectral bands of light reflected from the object are attenuated, and essentially only fluorescence emission is transmitted and detected by the image sensor. In phase 2, light reflected from the object is transmitted and detected by the image sensor.

In WO 2017/036600 A1 a fluorescence light detection system and a microscopy system are described (title; summary; page 1, first paragraph; page 3, first full paragraph) The fluorescence light detection system 19D has a beam splitter system 35D that directs light with wavelengths greater than a cutoff wavelength $\lambda_0$ to a first camera 21D and light with wavelengths less than the cutoff wavelength $\lambda_0$ to a second camera 23D (page 36, single whole paragraph; FIG. 6). The cutoff wavelength $\lambda_0$ can be in the range of 600 nm to 630 nm, whereby fluorescent light from fluorophore protoporphyrin IX is essentially transmitted exclusively to the first camera 21 (ibid.).

US 2019/0170647 A1 describes a mapping system (title, summary, paragraphs [0001], [0008]). A camera head 105c comprises a color separation prism 201c, a first image pickup element for picking up an image 1051a in visible light, a second image pickup element for picking up an image 1051b in visible light, and a third image pickup element for picking up an image 1052 in near infrared light (paragraphs [0139], [0150], FIG. 10). A dichroic film 223 of the color separation prism 201c reflects near infrared light to the third image pickup element and transmits visible light. A dichroic film 225 of the color separation prism 201c reflects red visible light to the first image pickup element and transmits blue and green visible light to the second image pickup element (ibid.).

SUMMARY OF THE INVENTION

An object of the present invention is to provide an improved image capturing device, an improved image capturing system and an improved method for capturing an image of an object of medical interest in remitted or reflected illumination light and for capturing an image of the object of interest in fluorescent light generated by at least one of Cy5.5 and SGM-101 and for capturing an image of the object in fluorescent light generated by at least one of OTL38 and indocyanine green.

An image capturing device for capturing an image of an object of medical interest in remitted or reflected illumination light and for capturing an image of the object in fluorescent light generated by at least one of Cy5.5 and SGM-101 and for capturing an image of the object in fluorescent light generated by at least one of OTL38 comprises a first image sensor detecting blue, green and red light, a second image sensor detecting fluorescent light of at least one of Cy5.5 and SGM-101 and of at least one of OTL38 and indocyanine green, a beam splitter guiding light emanating from the object and having a wavelength, which is smaller than a predetermined cutoff wavelength $\lambda_0$ within the red spectral range, to the first image sensor and for guiding light emanating from the object and having a wavelength greater than the predetermined cutoff wavelength $\lambda_0$ to the second image sensor, and a number of filters arranged upstream of the second image sensor for partially, substantially or completely suppressing light having a wavelength suitable for exciting at least one of Cy5.5 and SGM-101 and for partially, substantially or completely suppressing light having a wavelength suitable for exciting fluorescence of at least one of OTL38 and indocyanine green.

The image capturing device is designed and constructed for capturing images of an object of medical interest within a natural or artificial cavity or at an external surface of a body of a human or animal patient. For this purpose, the image capturing device has in particular mechanical, optical and electrical interfaces to other devices approved for use in operating theatres, treatment rooms and other medical facilities.

Furthermore, the image capturing device may be designed to be sterilizable, in particular autoclavable. For this purpose, the imaging device has, in particular, a fluid-tight or hermetically sealed outer surface and can be exposed to sterilizing media, e.g. steam at overpressure and 140° C., over a longer period of time without being damaged.

The image capturing device may be designed monocular, i.e. it may provide only one image signal representing a single image at any given time and in any spectral range or for each color channel. Alternatively, the image capturing device can be designed for the capture of stereo images, i.e. it can capture two images simultaneously in one and the same spectral range or for the same color channel and generate two image signals which represent these two captured images. This may apply to all spectral ranges or color channels or only to individual spectral ranges or color channels.

The image capturing device may include a camera which can be coupled to a standard eyepiece of an endoscope or an exoscope or a surgical microscope. Alternatively, the image capturing device itself may be an endoscope, in particular a video endoscope, an exoscope or a surgical microscope.

The image capturing device is, in particular, provided and designed for detecting fluorescence of at least one of Cy5.5 (in the spectral range from 680 nm to 720 nm, with a maximum at 694 nm or 707 nm) and SGM-101 (in the spectral range from 690 nm to 720 nm, with a maximum at 705 nm) and for detecting fluorescence of at least one of OTL38 (in the spectral range from 780 nm to 810 nm, with a maximum at 793 nm) and indocyanine green (in the spectral range from 780 nm to 870 nm, with a maximum at 830 nm).

The first image sensor is designed and constructed to detect light in the wavelength ranges perceived by the healthy human eye as blue, green and red. For this purpose, the first image sensor detects in particular both light in a wavelength range which is less than 490 nm and light in a wavelength range which is between 490 nm and 585 nm as well as light in a wavelength range of more than 585 nm. The first image sensor does not detect the entire wavelength range of 585 nm to 750 nm perceived by the healthy human eye as orange or red, and does not detect the entire wavelength range down to 380 nm perceived by the healthy human eye as violet or blue, or does not detect the latter wavelength range with constant sensitivity throughout.

For example, the beam splitter has a dichroic layer in a prism that is otherwise optically transparent. The cutoff wavelength $\lambda_0$ is the wavelength at which one half of the incident light is directed to the first image sensor and the other half is directed to the second image sensor.

The number of filters comprises one filter or two filters or even more filters arranged in close vicinity to each other (in particular on one surface of a transparent or reflecting object) or in locations spaced apart from each other. The number of filters suppresses light with a wavelength suitable for exciting fluorescence of at least one of Cy5.5 and SGM-101 and suppresses light with a wavelength suitable for exciting fluorescence of at least one of OTL38 and indocyanine green. For this purpose, the characteristics of the number of filters, i.e. the wavelength dependence of their transmission, are especially matched to the characteristics of the light source used to excite fluorescence of at least one of Cy5.5 and SGM-101 and to the characteristics of the light source used to excite fluorescence of at least one of OTL38 and indocyanine green, i.e. to the emission spectra of the light sources. The narrower the emission spectra of the light sources, the narrower the wavelength ranges that are suppressed by the number of filters. Light of a certain wavelength is suppressed by the number of filters if the intensity or flux of the light after passing through the number of filters is lower than before. Complete suppression, i.e. the complete removal of all photons of a certain wavelength, is an ideal case that is not always easily achieved in practice.

The number of filters can be located immediately upstream of the second image sensor, i.e. in the direction of propagation of the light to be detected immediately before the second image sensor, and thus between the beam splitter and the image sensor. The number of filters can, for example, be arranged at a light exit surface of the beam splitter or at a light entrance surface of the image sensor, i.e. directly in front of the light-sensitive layer of the image sensor. Alternatively, the number of filters can be arranged before the beam splitter in the direction of propagation of the light to be detected, for example between an objective lens and the beam splitter or even upstream of an objective lens. If the number of filters comprises more than one filter, the filters of the number of filters can be located at different locations.

Thus, the image capturing device has a first image sensor which may be largely or entirely similar or identical to a conventional image sensor for capturing an image in remitted or reflected white light. Thus, apart from limitations due to the absence of parts of the spectral range perceived by the healthy human eye as orange to red, which are, however, partially correctable, the first image sensor captures an ordinary color image in remitted or reflected white light.

Both fluorescent light originating from Cy5.5 or SGM-101 and fluorescent light originating from OTL38 or indocyanine green are detected by the second image sensor only. Fluorescence of at least one of Cy5.5 and SGM-101 and fluorescence of at least one of OTL38 and indocyanine green can be simultaneously excited and detected by the second image sensor.

If the second image sensor is a monochrome image sensor, i.e. has only one color channel, it is not possible to distinguish between fluorescent light from Cy5.5 or SGM-101 and fluorescent light from OTL38 or indocyanine green. In this case, alternating excitation of the fluorescence of Cy5.5 or SGM-101 and excitation of the fluorescence of OTL38 or indocyanine green allows images in fluorescent light of Cy5.5 or SGM-101 and images in fluorescent light of OTL38 or indocyanine green to be generated alternately.

If the second image sensor has separate color channels for capturing fluorescent light from Cy5.5 or SGM-101 and for capturing fluorescent light from OTL38 or indocyanine green, an image in fluorescent light from at least one of Cy5.5 and SGM-101 and an image in fluorescent light from at least one of OTL38 and indocyanine green can be captured simultaneously.

An image captured during a time interval without excitation of fluorescence by the second image sensor can be used to correct the red color channel of the first image sensor.

In particular, in an image capturing device as described herein, the cutoff wavelength $\lambda_0$ is smaller than the wavelength of the fluorescence maximum of at least one of Cy5.5 and SGM-101.

In particular, in an imaging device as described herein, the cutoff wavelength $\lambda_0$ of is not greater than 680 nm or 690 nm or 700 nm.

In particular, if the image capturing device is configured for the detection of fluorescence emanating from Cy5.5, the cutoff wavelength $\lambda_0$ of is not greater than 680 nm or 690 nm, and if the image capturing device is configured for the detection of fluorescence emanating from SGM-101, the cutoff wavelength $\lambda_0$ of is not greater than 690 nm or 700 nm. If the image capturing device is configured for the detection of both fluorescence emanating from Cy5.5 and fluorescence emanating from SGM-101, the cutoff wavelength $\lambda_0$ of is in particular 690 nm or close to 690 nm.

In particular, in an image capturing device as described herein, the cutoff wavelength $\lambda_0$ is not less than 610 nm or 620 nm or 630 nm and not greater than 680 nm or 690 nm or 700 nm.

The steeper the filter edge of the beam splitter is, the greater the cutoff wavelength $\lambda_0$ can be, i.e. the more completely the orange and red spectral range can be detected by the first image sensor. The smaller the cutoff wavelength $\lambda_0$ is, the greater the portion of fluorescent light of Cy5.5 or SGM-101 that is detected by the second image sensor and the less the distortion of the white light image detected by the first image sensor by fluorescent light of Cy5.5 or SGM-101.

In particular, in an image capturing device as described herein, the number of filters suppress light with a wavelength in the range of 740 nm to 810 nm.

In particular, in an image capturing device as described herein, the number of filters suppress light with wavelengths within an interval whose lower limit is not less than 700 nm or not less than 730 nm or not less than 750 nm or not less than 760 nm or not less than 770 nm and whose upper limit is not greater than 780 nm or not greater than 790 nm or not greater than 800 nm or not greater than 820 nm or not greater than 850 nm.

Within the wavelength interval, the intensity of light that passes through the filter is, for example, less than half, in particular less than one third or less than one fifth or less than one tenth the intensity before the filter. Outside the wavelength interval, the intensity of light that has passed the filter is, for example, more than half, in particular more than two-thirds or more than four-fifths or more than nine-tenths of the intensity before the filter. In reality, the filter edges, i.e., the rising or falling portions of the transmission curve at the boundaries of the interval, are not step functions, and the boundaries or the terms "inside" and "outside" therefore cannot be understood to the nanometer. The boundary could be defined as the midpoint of the rising or falling transmission curve at the ends of the interval, or even as the points of minimum or maximum transmission in the range of the ends of the interval. This is known to the person skilled in the art.

The narrower the band of light that excites the fluorescence of at least one of OTL39 and indocyanine green, the narrower the filter can be designed to suppress the detection of remitted or reflected excitation light by the second image sensor.

In particular, an image capturing device as described herein further comprises an objective at least either for forming an image of the object in illumination light remitted or reflected by the object or for forming an image of the object in fluorescent light emanating from the object.

In particular, in an image capturing device as described herein, the objective is provided and designed for producing an image of the object in illumination light reflected or reflected by the object and for producing an image of the object in fluorescent light emanating from the object, the beam splitter being arranged between the objective and the image sensors.

In this case, the lens is especially designed and constructed for imaging in the wavelength range below the cutoff wavelength $\lambda_0$ as well as for imaging in the wavelength range above the cutoff wavelength $\lambda_0$. The beam splitter is arranged downstream of the lens and upstream of the image sensors.

In particular, in an image capturing device as described herein, the number of filters substantially or completely suppress light having a wavelength suitable for exciting fluorescence of Cy5.5 or SGM-101.

In particular, in an image capturing device as described herein the number of filters suppress light having a wavelength in the range of 660 nm to 700 nm.

Light having wavelengths suitable for exciting fluorescence of Cy5.5 or SGM-101 can be suppressed for both image sensors. In this case, an image of the object in remitted or reflected illumination light and an image of the object in fluorescence light generated by at least one of Cy5.5 and SGM-101 can be captured simultaneously.

As an alternative, light having wavelengths suitable for exciting fluorescence of Cy5.5 or SGM-101 can be suppressed only by a filter (in particular the number of filters or one of the number of filters) arranged immediately upstream the second image sensor. In this case, if the cutoff wavelength $\lambda_0$ is between wavelengths exciting fluorescence of Cy5.5 or SGM-101 and wavelengths of fluorescence of Cy5.5 or SGM-101, a maximum portion of reflected or remitted illumination light is captured by the first image sensor—thereby facilitating a particularly natural color reproduction—but an image in reflected or remitted illumination light and an image in fluorescence light generated by Cy5.5 or SGM-101 cannot be captured simultaneously but need to be captured alternately in distinct time intervals.

In an image capturing device as described herein, the number of filters partially passes the suppressed light.

Suppression, i.e. reduction of the intensity of excitation light, can, if the excitation light has a higher intensity than the other light intended to illuminate the object, prevent the image captured by the first image sensor, in particular its red color channel, from being overexposed to remitted or reflected excitation light and enable a natural color impression to be obtained. A partial or extensive, but not complete suppression of the remitted or reflected excitation light can enable a particularly natural color reproduction.

In particular, an image capturing device as described here is provided and configured for capturing a stereo image.

For this purpose, the image capturing device comprises, for example, two first image sensors and two second image sensors, wherein one first image sensor and one second image sensor are provided and configured for capturing an image intended for reproduction for the left eye and one first image sensor and one second image sensor are provided and configured for capturing an image intended for reproduction for the right eye. Alternatively, each of the first image sensor and the second image sensor can be of such a size that an image intended for reproduction for the left eye and an image intended for reproduction with the right eye can be captured on them side by side.

An image capturing system for capturing an image of an object of medical interest in remitted or reflected illumination light and for capturing an image of the object in fluorescent light generated by at least one of Cy5.5 and SGM-101 and for capturing an image of the object in fluorescent light generated by at least one of OTL38 and indocyanine green, comprises a light source device for alternately or simultaneously generating illumination light in the blue, green and red wavelength range, first excitation light exciting fluorescence of at least one of Cy5.5 and SGM-101 and second excitation light exciting fluorescence of at least one of OTL38 and indocyanine green, and an image capturing device as described herein.

In particular, the light source device is provided and configured for alternately or simultaneously generating illumination light within the visible wavelength range below 630 nm or below 650 nm or below 680 nm or below 690 nm or below 700 nm and first excitation light in the wavelength range of 660 nm or 670 nm or 680 nm to 690 nm or 700 nm or 710 nm oe 720 nm and second excitation light in the wavelength range of 760 nm or 770 nm or 780 nm to 790 nm or 800 nm or 810 nm. In particular, the light source device has separately controllable light sources for each of generating the illumination light, generating the first excitation light and generating the second excitation light.

In particular, in an image capturing system as described here, the number of filters transmits a part of the remitted or reflected first excitation light to allow a natural color impression.

In particular, in an image capturing system as described herein, the light source device comprises a light-emitting diode or laser for generating excitation light having a wavelength in the range of 660 nm or 670 nm or 680 nm to 690 nm or 700 nm or 710 nm oe 720 nm and a light-emitting diode or laser for generating excitation light having a wavelength in the range of 760 nm or 770 nm or 780 nm to 790 nm or 800 nm or 810 nm.

A method of capturing an image of an object of medical interest in remitted or reflected illumination light and capturing an image of the object in fluorescent light generated by at least one of Cy5.5 and SGM-101 and capturing an image of the object in fluorescent light generated by at least one of OTL38 and at least one of OTL38 and indocyanine green comprises irradiating the object with illumination light in the blue, green and red spectral regions, irradiating the object with first excitation light for exciting fluorescence of at least one of Cy5.5 and SGM-101, irradiating the object with second excitation light for exciting fluorescence of at least one of OTL38 and indocyanine green, capturing a color image of the object in the blue, green and red spectral regions by a first image sensor, and capturing a fluorescence image of the object in the red and infrared spectral regions by a second image sensor, wherein reflected or remitted first excitation light is not or only partially detected by the second image sensor, wherein reflected or remitted second excitation light is not or only partially captured by the second image sensor.

In particular, the procedure is carried out with an image capturing device as described herein or with an image capturing system as described herein.

In particular, in a process such as that described herein, a number of filters upstream of the second image sensor suppresses remitted or reflected second excitation light partially, largely or completely.

In particular, in a process as described herein, the irradiation with illumination light in the blue, green and red spectral range, the irradiation with the first excitation light, the irradiation with the second excitation light, the capture of the color image in the blue, green and red spectral range by the first image sensor and the capture of the fluorescence image in the red and infrared spectral range by the second image sensor take place simultaneously at least at times.

Irradiation with illumination light in the blue, green and red spectral range, irradiation with the first excitation light, irradiation with the second excitation light, capture of the color image in the blue, green and red spectral range by the first image sensor and capture of the fluorescence image in the red and infrared spectral range by the second image sensor can take place completely simultaneously. As an alternative, for example, only the irradiation with illumination light in the blue, green and red spectral range and the capture of the color image in the blue, green and red spectral range by the first image sensor and the capture of an image in the red and infrared spectral range by the second image sensor take place simultaneously, whereby the image captured by the second image sensor can be used to correct a red color channel of the color image captured by the first image sensor. As a further alternative, irradiation with illumination light in the blue, green and red spectral range, irradiation with the first excitation light, capture of the color image in the blue, green and red spectral range by the first image sensor and capture of the fluorescence image in the red and infrared spectral range by the second image sensor take place simultaneously, but not the irradiation with the second excitation light, in order to simultaneously capture a color image and a fluorescence image exclusively in fluorescent light of at least one of Cy5.5 and SGM-101. Alternatively, irradiation with illumination light in the blue, green and red spectral range, irradiation with the second excitation light, capture of the color image in the blue, green and red spectral range by the first image sensor and capture of the fluorescence image in the red and infrared spectral range by the second image sensor are performed simultaneously, but not irradiating the first excitation light, to simultaneously capture a color image by the first image sensor and a fluorescence image exclusively in fluorescent light of at least one of OTL38 and indocyanine green by the second image sensor.

In particular, a method as described herein further comprises irradiating the object with illumination light in the blue, green and red spectral range or irradiating the object with red light in the red spectral range, capturing a red light image of the object in the red spectral region by the second image sensor while irradiating the object with illumination light in the blue, green and red spectral regions or with red light in the red spectral region, and correcting the red color channel of the color image based on the red light image.

In particular, in a procedure as described herein, the object is not irradiated with the second excitation light during the capture of the red light image.

In particular, in a procedure as described herein, the object is not irradiated with the first excitation light during the capture of the red light image.

These and other advantages and features of the invention will be apparent from the following description of representative embodiments, considered along with the accompanying drawings.

DETAILED DESCRIPTION OF REPRESENTATIVE EMBODIMENTS

Figure 1:
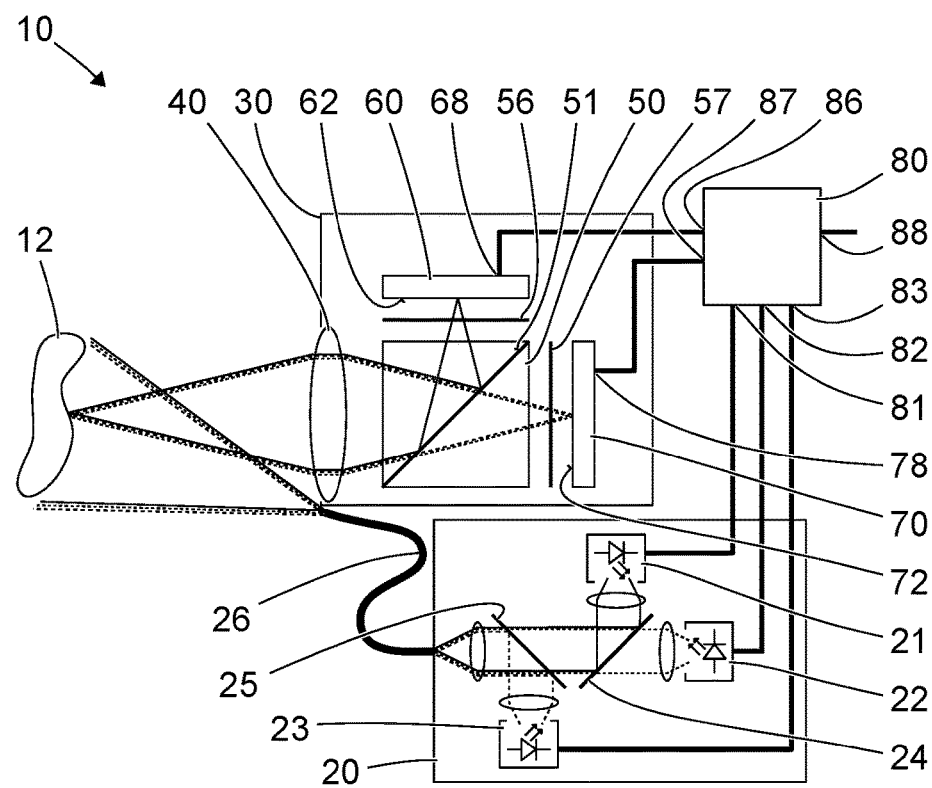
FIG. 1 is a schematic representation of an image capturing system.

FIG. 1 shows a schematic representation of an image capturing system 10 for capturing an image of an object of medical interest 12 in remitted or reflected illumination light, for capturing an image of the object in fluorescent light emanating from Cy5.5 or SGM-101, and for capturing an image in fluorescent light emanating from OTL38 or indocyanine green. The object 12 may be placed inside a cavity or at a surface of a body of a human or animal patient. Accordingly, the imaging system 10 may be located entirely or partially inside or entirely outside a body of a human or animal patient.

The image capturing system 10 may, for example, be an endoscope, exoscope or surgical microscope or may include an endoscope, exoscope or surgical microscope.

The observation of fluorescent light, in particular the observation of images in fluorescent light, can enable or simplify a diagnosis. Some fluorophores, when administered to a patient have a higher concentration in tumors than in healthy tissue, so that the fluorescence of one of these fluorophores can be used to differentiate between healthy tissue and neoplasia. Some fluorophores, for example indocyanine green, have a higher concentration in vessels, so that in the fluorescent light of one of these fluorophores, the vascular system can be particularly well distinguished from surrounding tissue. Some fluorophores facilitate the detection or differentiation of other tissue types, functions or dysfunctions.

The image capturing system 10 comprises a light source device 20 having a first light source 21, a second light source 22, a third light source 23, a first dichroic reflecting surface 24 and a second dichroic reflecting surface 25. In FIG. 1, it is suggested that each of the light sources 21, 22, 23 comprises a light emitting diode for generating light. Each light source 21, 22, 23 may alternatively or additionally comprise one or more semiconductor lasers or other lasers, further light-emitting diodes or other light sources.

The first light source 21 is for the generation of broadband illumination light, the spectrum of which has components in the wavelength range perceived as blue by the healthy human eye, in the wavelength range perceived as green by the healthy human eye and in the wavelength range perceived as orange to red by the healthy human eye. For this purpose, the first light source 21 comprises, for example, one or more light-emitting diodes originally emitting in the wavelength range perceived by the healthy human eye as blue or violet, and a luminescence layer which absorbs part of the blue or violet light and emits light in the wavelength ranges perceived by the healthy human eye as red and green. As an alternative, the first light source 21 has, for example, several light-emitting diodes, each emitting approximately monochromatic, i.e. narrow-band light at different wavelengths, which together cover the widest possible range of wavelengths between a lower limit at about 380 nm to 400 nm and an upper limit at about 700 nm to 750 nm.

The second light source 22 is provided and configured to emit narrow-band first excitation light for excitation of fluorescence of at least one of Cy5.5 and SGM-101. For this purpose, the second light source 22 emits light that is as narrow-banded as possible and as intense as possible within the wavelength range from approximately 660 nm to approximately 700 nm, for example at approximately 675 nm, the absorption maximum of Cy5.5, or at approximately 680 nm, the absorption maximum of SGM-101. The second light source 22 can be configured to emit excitation light exciting both fluorescence of Cy5.5 and the fluorescence of SGM-101.

The third light source 23 is provided and configured to emit narrow-band second excitation light for excitation of fluorescence of at least one of OTL38 and indocyanine green. For this purpose, the third light source 23 in particular emits light that is as narrow-band as possible and as intense as possible within the wavelength range between 700 nm and 850 nm, for example at approximately 774 nm or 776 nm, the absorption maximum of OTL38, or at approximately. 800 nm, the absorption maximum of indocyanine green. The third light source 23 can be configured to emit excitation light exciting both fluorescence of OTL38 and the fluorescence of indocyanine green.

The first dichroic reflecting surface 24 reflects illumination light emitted by the first light source 21 completely or as much as possible and transmits first excitation light emitted by the second light source 22 completely or as much as possible, so that the illumination light produced by the first light source 21 and the first excitation light produced by the second light source 22 are superimposed as completely as possible. The second dichroic reflecting surface 25 reflects second excitation light emitted by the third light source 23 completely or as much as possible and transmits illumination light generated by the first light source 21 and first excitation light generated by the second light source 22 completely or as much as possible, so that the illumination light generated by the first light source 21, the first excitation light generated by the second light source 22 and the second excitation light generated by the third light source 23 are superimposed as completely as possible. The light of the light sources 21, 22, 23 which is superimposed as completely as possible, i.e. combined, is coupled into a fiber optic cable 26 and directed onto the object 12.

The dichroic reflecting surfaces 24, 25 of light source device 20 are examples of devices for superimposing or combining the light produced by light sources 21, 22, 23. Alternatively, polarization-dependent reflecting surfaces or other devices may be used, especially when the light sources 21, 22, 23 produce polarized light.

The image capturing system 10 further comprises an image capturing device 30. The image capturing device 30 can be a camera or part of a camera. As an alternative, the image capturing device 30 can be an endoscope or an exoscope or a surgical microscope or part of an endoscope or an exoscope or a surgical microscope.

The image capturing device 30 comprises an objective 40 for imaging the object 12, i.e. for generating a real image of the object 12, and a beam splitter 50 with a dichroic reflecting surface 51 in a prism which is otherwise optically transparent. Downstream of the beam splitter 50, an optional first filter 56 is arranged in front of a first image sensor 60 and a second filter 57 is arranged in front of a second image sensor 70. The objective 40 generates real images of the object 12 in light-sensitive layers 62, 72 of the image sensors 60, 70. As an example, the light-sensitive layers 62, 72 of the image sensors 60, 70 are shown as surfaces of the image sensors 60, 70 facing the beam splitter 50.

The dichroically reflecting surface 51 of the beam splitter 50 causes an image of the object 12 in remitted or reflected illumination light from the first light source 21, hereinafter referred to as the color image, to be formed in the light-sensitive layer 62 of the first image sensor 60, and an image of the object 12 in fluorescent light emitted by the object 12, hereinafter referred to as the fluorescence image, to be formed in the light-sensitive layer 72 of the second image sensor 70. For this purpose, the dichroic reflecting surface 51 of the beam splitter 50 reflects substantially completely and substantially exclusively light with wavelengths smaller than a cutoff wavelength $\lambda_0$ and transmits substantially completely and substantially exclusively light with wavelengths larger than the cutoff wavelength $\lambda_0$. The cutoff wavelength $\lambda_0$ is in the range from 630 nm to 700 nm, in particular at 670 nm to 690 nm. As a result, part of the light remitted or reflected by the object 12 within the light perceived by the healthy human eye as orange or red falls on the first image sensor 60 and is detected in its red color channel. Therefore, the color image captured by the first image sensor 60 alone can produce an essentially normal or natural color impression.

Both fluorescent light generated by Cy5.5 or SGM-101 in the object 12 and fluorescent light generated by OTL38 or indocyanine green in the object 12 is detected by the second image sensor 70. The second image sensor 70 can be a monochromatic image sensor, i.e. it can have only one color channel. Alternatively, the second image sensor 70 can have several color channels, one of which exclusively or substantially exclusively detects the fluorescence of at least one of Cy5.5 and SGM-101 and another exclusively or substantially exclusively detects the fluorescence of at least one of OTL38 and indocyanine green.

The second filter 57 in front of the second image sensor 70 is provided and configured to suppress both first excitation light generated by the second light source 22 and remitted by the object 12. For this purpose, the second filter 57 suppresses in particular light in a wavelength range whose lower limit is at 650 nm to 670 nm and whose upper limit is at 690 nm to 710 nm, which is as narrow as possible and comprises the spectrum of the first excitation light generated by the second light source 22 as completely as possible.

Furthermore, the second filter 57 is provided and configured to suppress second excitation light generated by the third light source 23 and remitted by the object 12. For this purpose, the second filter 57 suppresses in particular light in a wavelength range whose lower limit is at 750 nm to 770 nm and whose upper limit is at 800 nm to 820 nm, which is as narrow as possible and comprises the spectrum of the second excitation light generated by the third light source 23 as completely as possible.

The second filter 57 may be designed to suppress only a large part, but not all, of the light produced by the second light source 22 and reflected or remitted by the object 12. Furthermore, the second filter 57 may be designed to suppress only a large part, but not all, of the light produced by the third light source 23 and reflected or remitted by the object 12. In this way, the remission or reflection characteristics of the object 12 at the wavelengths suppressed by the second filter 57 can also contribute to the formation of the color image in the light-sensitive layer 72 of the second image sensor 70.

The first image sensor 60 provides, at an image signal output 68, a first image signal representing the color image captured by the first image sensor 60. The second image sensor 70 provides, at an image signal output 78, a second image signal representing the fluorescence image captured by the second image sensor 70.

The image capturing system 10 further comprises a Camera Control Unit (CCU) 80 having a first control output 81 coupled to the first light source 21, a second control output 82 coupled to the second light source 22, a third control output 82 coupled to the third light source 23, a first image signal input 86 coupled to the image signal output 68 of the first image sensor 60, a second image signal input 87 coupled to the image signal output 78 of the second image sensor 70, and an image signal output 88. The camera control unit 80 controls the light sources 21, 22, 23 of the light source device 20 and the image sensors 60, 70, receives and processes the image signals provided by the image sensors 60, 70 and provides, at an image signal output 88, an image signal containing information from both image signals provided by the image sensors 60, 70.

In particular, the image signal provided by the camera control unit 80 at image signal output 88 represents a color image of the object in which tissue recognizable by the fluorescence of Cy5.5 or SGM-101 and/or vessels or other structures or tissue characteristics recognizable by the fluorescence of OTL38 or indocyanine green are highlighted. The highlighting can be done by color, intensity or a time-dependent modulation for example.

Figure 4:
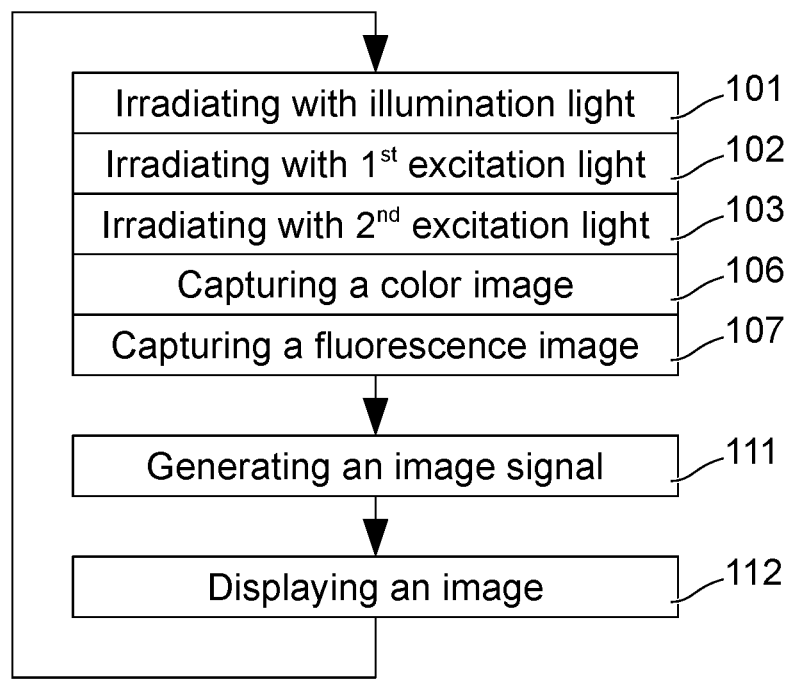
FIG. 4 is a schematic flowchart of a method of capturing images.
Figure 5:
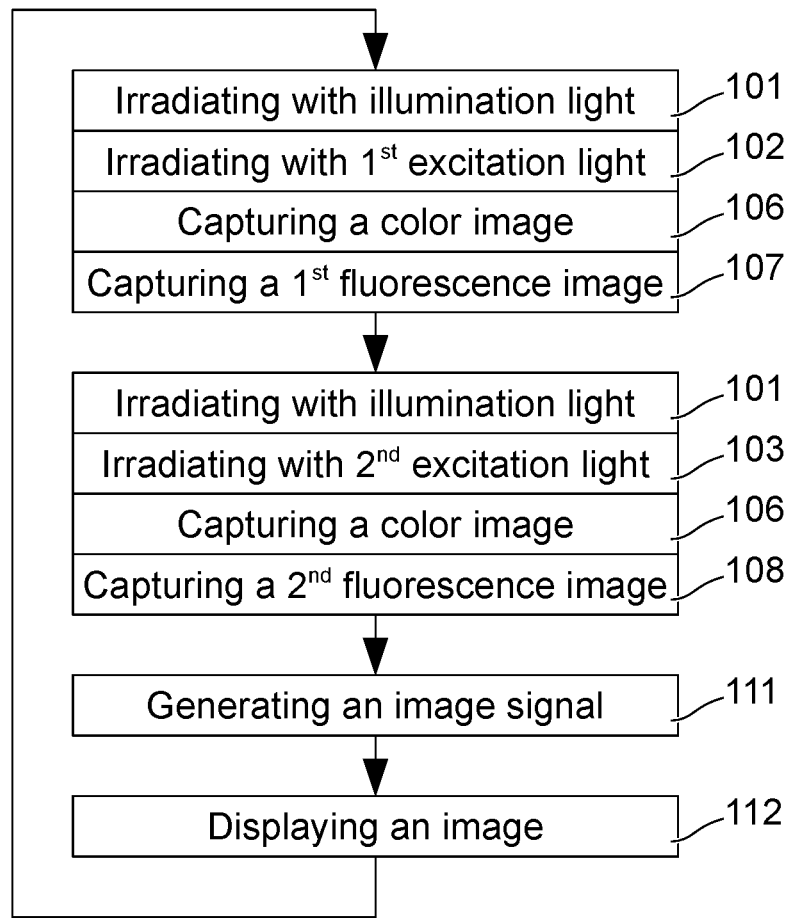
FIG. 5 is a schematic flowchart of another method of capturing images.
Figure 6:
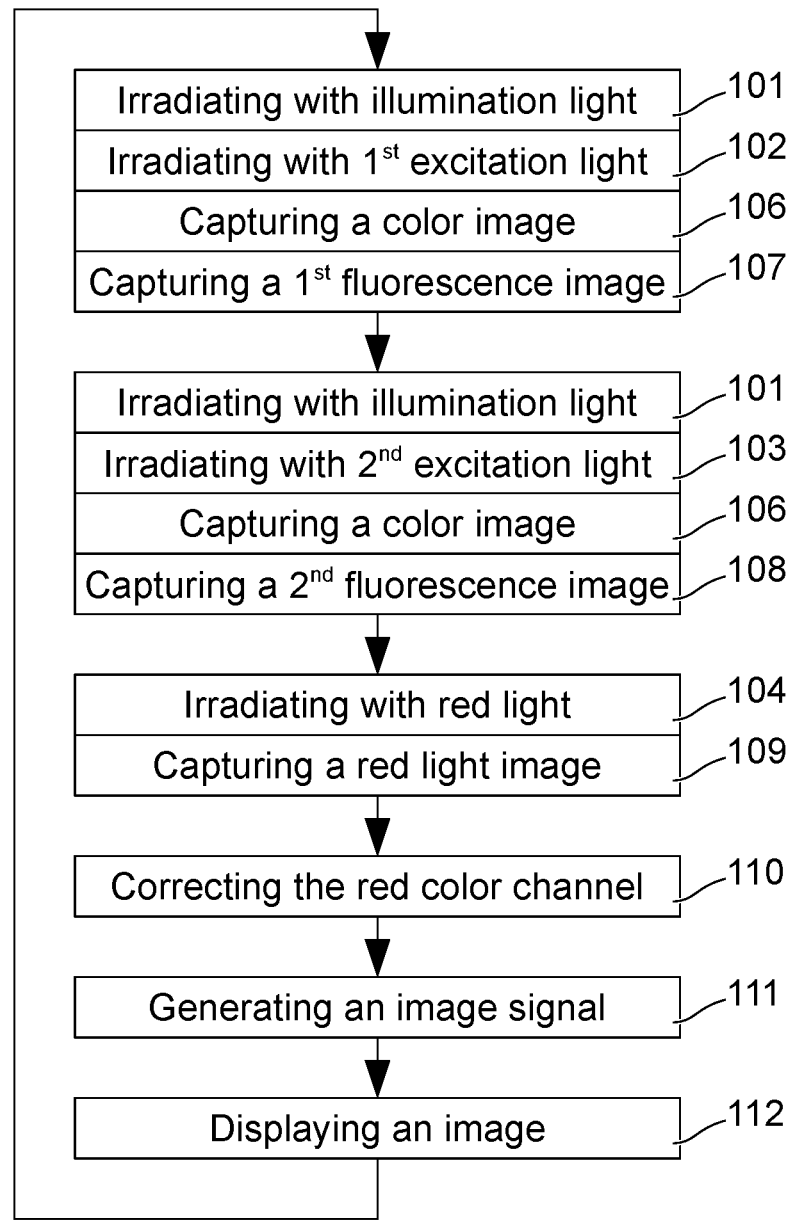
FIG. 6 is a schematic flowchart of another method of capturing images.

In particular, the camera control unit 80 controls one of the processes illustrated in FIGS. 4, 5 and 6.

Figure 2:
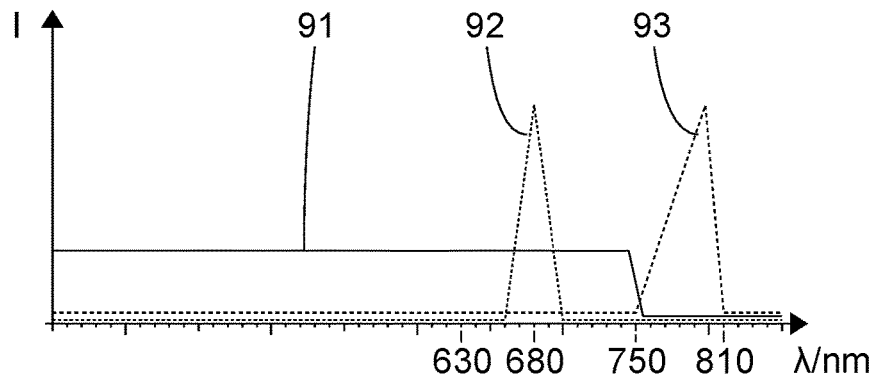
FIG. 2 is a schematic representation of spectra generated by a light source device of the imaging system shown in FIG. 1.

FIG. 2 shows a schematic representation of the emission spectra of the light sources 21, 22, 23. The wavelength in nm is assigned to the abscissa, the intensity I in arbitrary or relative units is assigned to the ordinate.

The spectrum 91 of the first light source 21 (cf. FIG. 1) or of the illumination light provided by the first light source 21, shown in a solid line, essentially comprises wavelengths between 350 nm and 750 nm and is essentially constant, i.e. wavelength-independent, between these limits in the example shown.

The spectrum 92 of the second light source 22 or of the first excitation light provided by the second light source 22, shown in a short dashed line, is narrowband. In the example shown, the spectrum 92 of the second light source 22 has a maximum at 675 nm or 680 nm.

The spectrum 93 of the third light source 23, i.e. of the second excitation light produced by the third light source 23, is shown in a longer dashed line and is narrowband. In the example shown, the spectrum 93 of the third light source has a maximum at about 770 nm to 800 nm.

Figure 3:
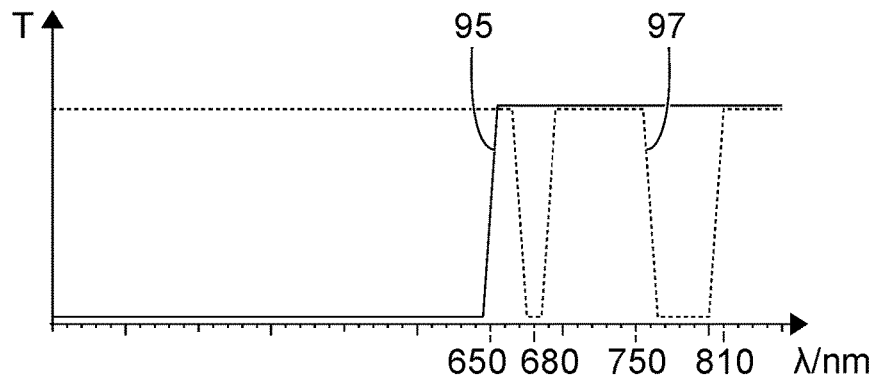
FIG. 3 is a schematic representation of spectral characteristics of a beam splitter and filters of the imaging system shown in FIG. 1.

FIG. 3 shows a schematic representation of the transmission characteristics of the dichroic surface 51 of the beam splitter 50 and the filters 56, 57 (cf. FIG. 1). The wavelength in nm is assigned to the abscissa, the transmission T is assigned to the ordinate.

The transmission 95 of the dichroic reflecting surface 51 of the beam splitter 50, shown in a solid line, is low, i.e. essentially 0, at wavelengths less than a cutoff wavelength $\lambda_0$ of about 650 nm, and high, i.e. essentially 1=100%, at wavelengths greater than the cutoff wavelength $\lambda_0$ of 650 nm. The reflection R not shown is complementary to the transmission 95, i.e. it is approximately R=1−T.

The transmission 97 of the second filter 57, shown in a longer dashed line, in front of the second image sensor 70 is low, in particular substantially 0, in a wavelength range between about 670 nm and about 690 nm in order to completely or substantially completely suppress first excitation light generated by the second light source 22 and reflected or remitted by the object 12. Furthermore, the transmission 97 is low, in particular substantially 0, in a wavelength range between about 760 nm and about 800 nm or 810 nm in order to completely or substantially completely suppress second excitation light generated by the third light source 23 and reflected or remitted by the object 12. At wavelengths greater than about 800 nm or 810 nm and at wavelengths between about 690 nm and about 760 nm, the transmission 97 of the second filter 57 is high, in particular substantially 1=100%. In the example shown, the transmission 97 of the second filter 57 is also high at wavelengths below about 670 nm, in particular essentially 1.

Both the spectra 91, 92, 93 of the light sources 21, 22, 23 and the transmission spectra 95, 97 may be slightly shifted with respect to the wavelengths shown in FIGS. 2 and 3. However, the spectra 92, 93 of the second light source 22 and the third light source 23 should be selected in such a way that the fluorescence of Cy5.5 and/or SGM-101 and the fluorescence of OTL38 and/or indocyanine green are excited as efficiently and as narrowly as possible. Furthermore, the transmission spectrum 95 and the complementary reflection spectrum of the beam splitter 50 are to be selected in such a way that as much as possible of the illumination light generated by the first light source 21, but as little as possible, in particular no, fluorescence light generated by Cy5.5 or SGM-101 or OTL38 or indocyanine green falls on the first image sensor 60. Furthermore, the transmission spectrum 97 of the second filter 57 is to be selected in such a way that both first excitation light generated by the second light source 22 and reflected or remitted by the object 12 and second excitation light generated by the third light source 23 and reflected or remitted by the object 12 falls on the second image sensor 70 to the smallest possible extent.

As an alternative to the spectra represented in FIG. 2, the spectrum 91 of the illumination light provided by the first light source 21 can provide a lower or much lower or even vanishing intensity at wavelengths greater than the cutoff wavelength $\lambda_0$. In this case, the second image sensor 70 receives little or no remitted or reflected illumination light, but mainly or exclusively fluorescent light.

As a further alternative, the cutoff wavelength $\lambda_0$ can be higher. In particular, the cutoff wavelength $\lambda_0$ can be set to about 690 nm which is between the maximum of the spectrum 92 of the second light source 22 and the maximum of the intensity of the fluorescent light emitted by Cy5.5 and/or SGM-101. In this case, the second filter 57 is not required to suppress the first excitation light. If the first filter 56 suppresses the first excitation light, a color image can be captured simultaneously with the first fluorescence image.

The second filter 57 can comprise a plurality of filters, wherein each filter of the plurality of filters can be embodied by one or more layers or films on the very same transparent substrate or on different substrates. For instance, one filter of the plurality of filters suppresses the first excitation light, and one filter of the plurality of filters suppresses the second excitation light.

Each of the first filter 56 and the second filter 57 can be located upstream the lens 40 or between the lens 40 and the beam splitter 50. If the second filter 57 comprises a plurality of filters, one or more of the plurality of filters can be located upstream the lens 40 or between the lens 40 and the beam splitter 50 and one or more of the plurality of filters can be located between the beam splitter 50 and the second image sensor 70.

FIG. 4 shows a schematic flowchart of a method of capturing an image of an object of medical interest 12 in remitted or reflected illumination light, of capturing an image of the object 12 in fluorescent light generated by at least one of Cy5.5 and SGM-101, and of capturing an image of the object in fluorescent light generated by at least one of OTL38 and indocyanine green. In particular, the method can be carried out with the image capturing system 10 shown in FIGS. 1 to 3 and controlled by the camera control unit 80 of the image capturing system 10, but alternatively also with a system having features, properties and functions differing from the image capturing system shown in FIGS. 1 to 3. Reference signs from FIGS. 1 to 3 are used as examples.

In a method step 101, the object 12 is irradiated with illumination light with a broad spectrum 91, which comprises components in the wavelength ranges perceived by the healthy human eye as blue, green and orange to red. In a further method step 102 carried out at the same time, the object 12 is irradiated with the first excitation light to excite the fluorescence of at least one of Cy5.5 and SGM-101. In a further method step 103 carried out simultaneously, the object 12 is irradiated with second excitation light for exciting the fluorescence of at least one of OTL38 and indocyanine green. In a further method step 106 carried out at the same time, a color image in remitted and reflected illumination light in the spectral ranges perceived by the healthy human eye as blue, green and orange to red is captured by a first image sensor 60. In a further method step 107 carried out simultaneously, an image of the object 12, referred to as a fluorescence image, in fluorescent light generated by at least one of Cy5.5 and SGM-101 and/or in fluorescent light generated by at least one of OTL38 and indocyanine green is captured by a second image sensor 70. The fluorescence of at least one of Cy5.5 and SGM-101 and the fluorescence of at least one of OTL38 and indocyanine green can be detected together in a monochrome fluorescence image or in two different color channels of a fluorescence image.

In a further method step 111, an image signal is generated which contains both information from the color image and information from the fluorescence image.

In a further method step 112, an image is displayed, controlled by the image signal generated in the method step 111, for example by one or more screens, a projector and/or VR (virtual reality) glasses.

Deviating from the illustration in FIG. 4, it is not necessary to generate the broadband illumination light and the first excitation light and the second excitation light simultaneously and to capture the color image and the fluorescence image simultaneously. Especially when the fluorescence image is captured by a monochrome image sensor 70 having only one color channel in which both the fluorescence of at least one of Cy5.5 and SGM-101 and the fluorescence of at least one of OTL38 and indocyanine green is detected, only partial simultaneity may be advantageous to distinguish the fluorescence of at least one of Cy5.5 and SGM-101 and the fluorescence of at least one of OTL38 and indocyanine green. Furthermore, only partial simultaneity, deviating from the representation in FIG. 4, can allow correction of the image signal in the red color channel and thus allow better color rendering. Examples of such modified methods are shown in FIGS. 5 and 6.

FIG. 5 shows a schematic diagram of a flow chart of a further method of capturing an image of an object of medical interest 12 in remitted or reflected broadband illumination light, of capturing an image of the object in fluorescent light generated by at least one of Cy5.5 and SGM-101 and of capturing an image of the object in fluorescent light generated by at least one of OTL38 and indocyanine green.

The method shown in FIG. 5 differs from the method shown in FIG. 4 in that initially, in a first time interval, only the irradiation 101 with illumination light, the irradiation 102 with first excitation light, the capture 106 of a color image and the capture 107 of a first fluorescence image (namely in fluorescence light generated by at least one of Cy5.5 and SGM-101) are performed simultaneously, but not the irradiation with the second excitation light. Only in a subsequent, non-overlapping second time interval does simultaneous irradiation 101 with broadband illumination light, irradiation 103 with second excitation light, capture 106 of a color image and capture 108 of a second fluorescence image (namely in fluorescence light produced by at least one of OTL38 and indocyanine green) take place, but not irradiation with first excitation light. In this way it is possible to distinguish between the fluorescence of Cy5.5 and/or SGM-101 and the fluorescence of OTL38 and/or indocyanine green, and in the image signal generated in subsequent step 111 and the image displayed under control thereby in subsequent step 112, the fluorescence of Cy5.5 and/or SGM-101 and the fluorescence of OTL38 and/or indocyanine green can be identified or marked or highlighted differently.

As an alternative deviating from FIG. 5, only the steps 101, 102, 106, 107 and thereafter the steps 111, 112 are conducted in order to capture an image of the object 12 in remitted or reflected illumination light and an image of the object 12 in fluorescent light generated by at least one of Cy5.5 and SGM-101, but no image of the object 12 in fluorescent light generated by OTL38 and/or OTL38. As a further alternative deviating from FIG. 5, only the steps 101, 103, 106, 108 and thereafter the steps 111, 112 are conducted in order to capture an image of the object 12 in remitted or reflected illumination light and an image of the object 12 in fluorescent light generated by at least one of OTL38 and indocyanine green, but no image of the object 12 in fluorescent light generated by Cy5.5 or SGM-101.

FIG. 6 shows a schematic flowchart of a further method of capturing an image of an object of medical interest in remitted or reflected broadband illumination light, of capturing an image of the object in fluorescent light generated by at least one of Cy5.5 and SGM-101, and of capturing an image of the object in fluorescent light generated by at least one of OTL38 and indocyanine green.

The method shown in FIG. 6 differs from the method shown in FIG. 5 in particular in that in a third time interval the object 12 is simultaneously irradiated with red light, i.e. light in the wavelength range perceived as red by the healthy human eye, and a red light image in remitted or reflected red light is captured by the second image sensor without simultaneously irradiating the object 12 with first excitation light or with second excitation light. Thereby, in one method step 109 only the red light remitted or reflected by the object 12 is detected—in the image capturing system shown in FIGS. 1 to 3: by the second image sensor 70—but not fluorescence. The red light image can be used in a subsequent step 110 to correct the red color channel of the color image and thus improve color reproduction. Instead of irradiation with red light, i.e. light that only has spectral components in the wavelength range perceived as red by the healthy human eye, light can be used that covers other wavelength ranges, for example broadband illumination light as used in step 101. In this case, the object 12 can be continuously exposed to the broadband illumination light having portions in the wavelength ranges perceived by the healthy human eye as blue, green, and red.

The method shown in FIG. 6 involves capturing a first fluorescence image and capturing a second fluorescence image at two different and non-overlapping time intervals, similar to the method shown in FIG. 5. Alternatively, similar to the method shown in FIG. 4, the fluorescence of at least one of Cy5.5 and SGM-101 and the fluorescence of at least one of OTL38 and indocyanine green can be detected simultaneously.

In each of the methods described with reference to the FIGS. 4 through 6, in the steps 107, 108, the second image sensor 70 can receive and detect both remitted and reflected illumination light and fluorescent light generated by at least one of Cy5.5 and SGM-101 and/or by at least one of OTL38 and indocyanine green. If the object 12 is continuously irradiated by illumination light generated by the first light source 21, a pure fluorescence image can be obtained as a difference between an image captured by the second image sensor during irradiation with both illumination light and excitation light and an image captured by the second image sensor during illumination with illumination light only.

If the object 12 is not continuously irradiated by illumination light generated by the first light source 21, a pure fluorescence image can be captured while the object 12 is illuminated with excitation light only.

As outlined above, the intensity of the illumination light generated by the first light source 21 can—different from the spectrum shown in FIG. 2—be small or can even vanish at wavelengths greater than the cutoff wavelength $\lambda_0$. In this case, the second image sensor 70 receives little or no illumination light generated by the first light source 21 and remitted or reflected by the object, even if the first light source 21 continuously generates illumination light. Rather, most or all of the light received by the second image sensor 70 is fluorescent light, and the image captured by the second image sensor 70 is a pure or almost pure fluorescence image.

If the illumination light generated by the first light source 21 provides only a low or a vanishing intensity at wavelengths above the cutoff wavelength $\lambda_0$, the methods described above with reference to the FIGS. 4 through 6 can be particularly advantageous. In this case, in the method described with reference to FIG. 6, in particular a fourth light source is provided for the generation of light in the wavelength range above the cutoff wavelength $\lambda_0$ in order to illuminate the object 12 in this wavelength range in the method step 104.

Figure 7:
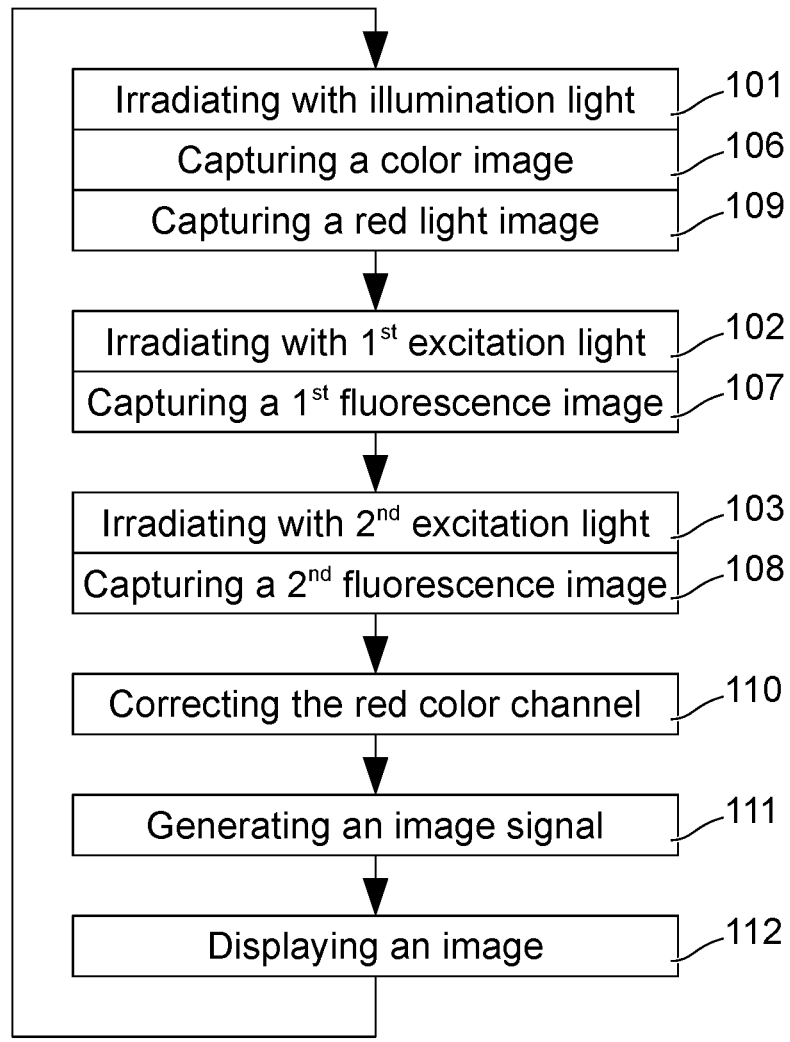
FIG. 7 is a schematic flowchart of another method of capturing images.

FIG. 7 shows a schematic flowchart of a further method of capturing an image of an object of medical interest in remitted or reflected broadband illumination light, of capturing an image of the object in fluorescent light generated by at least one of Cy5.5 and SGM-101, and of capturing an image of the object in fluorescent light generated by at least one of OTL38 and indocyanine green.

In particular, the method shown in FIG. 7 differs from the methods described with reference to the FIGS. 4 through 6 in that capturing 106 the color image, capturing 107 the first fluorescence image and capturing 108 the second fluorescence image are conducted in three different and non-overlapping time intervals.

In a first time interval, the object 12 is irradiated with illumination light, and simultaneously a color image is captured by the first image sensor 60. If the illumination light provides a relevant intensity in the wavelength range detected by the second image sensor 70, a red light image can be captured by the second image sensor 70 in an optional method step 109. In a later method step 110, this red light image can be used to correct the red color channel of the color image captured by the first image sensor 60.

In a second time interval, the object 12 is irradiated with first excitation light, and simultaneously a first fluorescence image in fluorescent light generated by at least one of Cy5.5 and SGM-101 is captured by the second image sensor 70.

In a third time interval, the object 12 is irradiated 103 with second excitation light, and simultaneously a second fluorescence image in fluorescent light generated by at least one of OTL38 and Indocyanine green is captured 108 by the second image sensor 70.

In particular, an image capturing system 10 as described with reference to the FIGS. 1 through 3 can provide several different modes of operation in which the methods described with reference to the FIGS. 4 through 7 or parts of these methods and/or further methods are conducted. In particular, each of the methods described with reference to FIGS. 5 and 6 can be modified either by omitting the method steps 101, 102, 106, 107 conducted in the first time interval or by omitting the method steps 101, 103, 106, 108 conducted in the second time interval. Furthermore, the image capturing system 10 can provide one or more modes of operation in which only a white light image is captured and/or only a white light image is displayed without any fluorescence information. Furthermore, the image capturing system 10 can provide one or more modes of operation in which only a fluorescence image is captured and/or only a fluorescence image is displayed without any white light image information.

The invention claimed is:

1. A method for capturing an image of an object of medical interest in remitted or reflected illumination light and capturing an image of the object in fluorescent light generated by at least one of Cy5.5 and SGM-101 and capturing an image of the object in fluorescence light generated by at least one of OTL38 and indocyanine green, comprising the steps of:

irradiating the object with illumination light in the blue, green and red spectral range;

irradiating the object with first excitation light exciting fluorescence of at least one of Cy5.5 and SGM-101;

irradiating the object with second excitation light exciting fluorescence of at least one of OTL38 and indocyanine green;

capturing a color image of the object in the blue, green and red spectral range by a first image sensor;

irradiating the object with illumination light in the blue, green and red spectral range or irradiating with red light in the red spectral range;

capturing a red light image of the object in the red spectral range by the second image sensor during irradiation of the object with illumination light in the blue, green and red spectral range or with red light in the red spectral range;

correcting the red color channel of the color image on the basis of the red light image; and capturing a fluorescence image in the red and infrared spectral range, by a second image sensor, wherein reflected or remitted first excitation light is not or only partially detected by the second image sensor, wherein reflected or remitted second excitation light is not or only partially detected by the second image sensor, and wherein the object is not irradiated with the second excitation light during capture of the red light image.

2. The method for capturing an image of an object of medical interest of claim 1, wherein the step of irradiating with illumination light in the blue, green and red spectral range, the step of irradiating with the first excitation light, the irradiating with the second excitation light, the step of capturing the color image in the blue, green and red spectral range by the first image sensor, and the step of capturing the fluorescence image in the red and infrared spectral range by the second image sensor take place at least at times simultaneously.

3. The method for capturing an image of an object of medical interest of claim 1, wherein the object is not irradiated with the first excitation light during capture of the red light image.

\* \* \* \* \*